United States Patent
Le Blanc (10) Patent No.: US 10,280,206 B2
(45) Date of Patent: May 7, 2019

(54) METHODS FOR PROTEIN AND PEPTIDE REDUCTION

(71) Applicant: DH Technologies Development PTE Ltd., Singapore (SG)

(72) Inventor: Yves Le Blanc, Newmarket (CA)

(73) Assignee: DH Technologies Development Pte. Ltd., Singapore (SG)

( * ) Notice: Subject to any disclaimer, the term of this patent is extended or adjusted under 35 U.S.C. 154(b) by 0 days.

(21) Appl. No.: 15/540,829

(22) PCT Filed: Dec. 18, 2015

(86) PCT No.: PCT/IB2015/059788
§ 371 (c)(1),
(2) Date: Jun. 29, 2017

(87) PCT Pub. No.: WO2016/108135
PCT Pub. Date: Jul. 7, 2016

(65) Prior Publication Data
US 2017/0362294 A1    Dec. 21, 2017

Related U.S. Application Data

(60) Provisional application No. 62/098,659, filed on Dec. 31, 2014.

(51) Int. Cl.
| | | |
|---|---|---|
| *C12N 9/00* | (2006.01) | |
| *C07K 14/62* | (2006.01) | |
| *C07K 16/00* | (2006.01) | |
| *G01N 30/06* | (2006.01) | |
| *G01N 30/12* | (2006.01) | |
| *G01N 30/30* | (2006.01) | |
| *G01N 30/72* | (2006.01) | |
| *G01N 30/88* | (2006.01) | |
| *G01N 33/68* | (2006.01) | |

(52) U.S. Cl.
CPC ............ *C07K 14/62* (2013.01); *G01N 30/06* (2013.01); *G01N 30/12* (2013.01); *G01N 30/30* (2013.01); *G01N 30/72* (2013.01); *G01N 30/7233* (2013.01); *C07K 16/00* (2013.01); *C12N 9/00* (2013.01); *G01N 33/68* (2013.01); *G01N 2030/067* (2013.01); *G01N 2030/8831* (2013.01)

(58) Field of Classification Search
CPC .. G01N 30/06; G01N 2030/067; G01N 30/12; G01N 30/30; G01N 30/72; G01N 30/7233; G01N 33/68; C07K 14/62; C07K 16/00; C12N 9/00
See application file for complete search history.

(56) References Cited

U.S. PATENT DOCUMENTS

| | | |
|---|---|---|
| 7,052,916 B2 | 5/2006 | Johnson |
| 8,633,300 B2 | 1/2014 | Ostergaard et al. |
| 2004/0053356 A1 | 3/2004 | Duewel et al. |
| 2005/0233406 A1 | 10/2005 | Woods, Jr. |
| 2006/0094121 A1 | 5/2006 | Reid et al. |
| 2006/0287834 A1 | 12/2006 | Kearney et al. |

FOREIGN PATENT DOCUMENTS

| | | | | |
|---|---|---|---|---|
| WO | WO2006/060083 | * | 6/2006 | ............ C07K 1/113 |
| WO | 2009018307 A2 | | 2/2009 | |

OTHER PUBLICATIONS

Mhatre et al. Strategies for Locating Disulfide Bonds in a Monoclonal Antibody via Mass Spectrometry. Rapid Commun Mass Spectrom, 1999. vol. 13, pp. 2503-2510. (Year: 1999).*

International Search Report and Written Opinion for PCT/IB2015/059788 dated Apr. 19, 2016.

Melissa Alvarez et al. "On-line Characterization of monoclonal antibody variants by liquid chromatography mass spectrometry operating in a two-dimensional format", Analytical Biochemistry, Elsevier, vol. 419, No. 1, Jul. 27, 2011 pp. 17-25.

Bao Quoc Tran et al. "On-Line multitasking analytical proteomics: How to separate, reduce, aklylate and digest whole proteins in an on-Line multidimensional chromatography system coupled to MS", Journal of Separation Science, vol. 31, No. 16-17 Sep. 10, 2008, pp. 2913-2923.

* cited by examiner

*Primary Examiner* — Marcela M Cordero Garcia (57) ABSTRACT

Methods and systems are provided herein for on-line preparation of a sample for mass spectrometry. In accordance with various aspects of applicant's teachings, the methods and systems can provide for the reduction of a polypeptide, for example, on a liquid chromatography column and can reduce or eliminate the need to incubate the reducing agent with the polypeptide and/or expose the reduced polypeptide to an alkylating agent.

19 Claims, 8 Drawing Sheets

Specification includes a Sequence Listing.

METHODS FOR PROTEIN AND PEPTIDE REDUCTION

RELATED APPLICATIONS

This application claims the benefit of priority from U.S. Provisional Application Ser. No. 62/098,659, filed on Dec. 31, 2014, the entire content of which is incorporated by reference herein.

FIELD

The present teachings generally relate to liquid chromatography/mass spectrometry (LC/MS), and more particularly to methods and systems for on-line reduction of polypeptides during liquid chromatography.

BACKGROUND

Protein and peptide analysis using liquid chromatography/mass spectrometry (LC/MS) applications can be challenging, time consuming, and/or expensive using traditional techniques for sample preparation. For example, challenges occur when sample preparation or analysis require multiple steps, since each additional step can add additional time to the sample preparation and potentially introduce errors to the analysis. Additional steps can also result in a loss of product, i.e., the peptide or protein of interest. This loss can occur, for example, during each transfer of the solution containing the protein or peptide prior to LC and/or mass spectrometric analysis, thereby resulting in decreased sensitivity/resolution.

Though denaturing a peptide or protein can improve mass spectral detection as a result of increased charging and exposure of ionisable groups (e.g., cleaving the disulfide bridges in a peptide or protein, followed by an alkylation step to ensure that the reduced disulfide bonds will not reform), such a reduction of disulfide bonds typically require an incubation step, which can decrease throughput and increase the complexity of sample preparation. Furthermore, incubation conditions can lead to alteration of side chain residue of protein and peptides, thus further complicating the analysis and interpretation. For example, while the length of the incubation period depends on reducing agent used, a 30 to a 60 minute time period is typically required and controlled conditions (e.g., pH) need to be carefully considered to avoid side reactions. Moreover, the incubation period is typically followed by the addition of alkylating agent to prevent the reformation of the disulfide bonds, which can lead to disulfide bond scrambling. Iodoacetamide, for example, is commonly added after reduction of the peptide, but is light sensitive and typically adds an additional 30 minutes of reaction time to the sample preparation process.

Accordingly, there remains a need for improved methods and systems for the reduction of peptides and proteins for their mass spectrometric analysis.

SUMMARY

The present teachings provide for methods and systems for the on-line reduction of polypeptides (e.g., proteins and peptides) using liquid chromatography. In accordance with various aspects of the present teachings, the methods include reducing a polypeptide retained on a liquid chromatography (LC) column, wherein one or more disulfide bonds are cleaved by a reducing agent, to prepare the reduced polypeptide for further analysis in downstream applications (e.g., mass spectrometry). In accordance with various aspects of applicant's teachings, the methods and systems can reduce or eliminate the need to incubate the reducing agent with the polypeptide and/or expose the reduced polypeptide to an alkylating agent (e.g., a thiol capping compound).

In accordance with one aspect, a method for on-line preparation of a sample for mass spectrometry analysis is provided that comprises introducing a sample containing (or suspected of containing) a polypeptide having at least one disulfide bond to a liquid chromatography column, wherein the liquid chromatography column is configured to fluidly couple to an ion source of a mass spectrometer. The method further comprises retaining the polypeptide on the liquid chromatography column, flowing a solution comprising a reducing agent through the liquid chromatography column so as to cleave one or more of the at least one disulfide bonds of the retained polypeptide while the reducing solution is flowed therethrough, and flowing an eluent through the liquid chromatography column so as to elute the reduced polypeptide from the liquid chromatography column. The method can further comprise delivering the eluate containing the reduced polypeptide to the ion source.

In another aspect, the present teachings provide a method of reducing a polypeptide in a sample. The method comprises introducing a sample comprising the polypeptide having one or more disulfide bonds capable of being reduced to a liquid chromatography column, retaining the polypeptide on the liquid chromatography column, and flowing a solution comprising a reducing agent through the liquid chromatography column at a first flow rate. The method can further comprise flowing an eluent through the LC column so as to elute the reduced polypeptide from the liquid chromatography column at a second flow rate. The method can further comprise delivering the eluate containing the reduced polypeptide to an ion source (e.g., a mass spectrometer).

In some aspects of the methods described herein, the solution comprising the reducing agent is flowed through the liquid chromatography column at a first fluid flow rate and the eluent is flowed through the liquid chromatography column at a second fluid flow rate, the second fluid flow rate being greater than the first fluid flow rate. In some aspects, the first and second fluid flow rates can be non-zero. For example, the first fluid flow rate can be in a range from about 50 μl/min to about 500 μl/min, and the second fluid flow rate can be about 50 μl/min to about 500 μl/min.

In some aspects of the present teachings, the LC column can be maintained at a temperature greater than about 37° C. (e.g., greater than about 40° C.). In some aspects, the solution comprising the reducing agent can have a temperature of about 60° C. to about 75° C.

In some aspects of the methods described herein, the solution can be buffered. For example, in certain aspects, the buffered solution has a pH of about 7. As an additional example, the buffered solution has a pH of between 7 and 8. In other aspects, the eluent can have a pH less than about 7.

In some aspects of the methods described herein, an outlet flow from the liquid chromatography column can be substantially continuous during the flowing steps. For example, the methods described herein can enable the reduction of a polypeptide without an incubation period. That is, the method can lack an incubation period after introducing the reducing solution into the LC column.

In some aspects, the eluent is flowed through the LC column without exposing the reduced polypeptide to one or more of an alkylating agent (e.g., iodoacetamide).

In some aspects of the methods described herein, the polypeptide having at least one disulfide bond comprises a protein (e.g., an enzyme). In other aspects, the polypeptide comprises a peptide. In one aspect, the polypeptide can comprise insulin. In some aspects, the polypeptide comprises an antibody (e.g., a monoclonal antibody) or an antibody-drug conjugate.

In various aspects, the solution comprising the reducing agent comprises a dithiol reducing agent (e.g., dithiothreitol (DTT)), tris(2-carboxyethyl)phosphine (TCEP), 2-mercaptoethanol (BME), and 2-mercaptoethanolamine (2-MEA), all by way of non-limiting example. In one aspect of the methods described herein, flowing a solution comprising a reducing agent comprises introducing a plug (bolus) of DTT into a fluid stream flowing through the liquid chromatography column at a first fluid flow rate.

In accordance with various aspects, certain embodiments of the applicant's teachings relate to a kit for reducing a peptide on an LC column prior to introduction into a mass spectrometer, the kit comprising one or more of an LC column, reagents for associating the peptides with the LC column, reducing reagents for cleaving one or more disulfide bonds of the peptide to be reduced, and an eluent for eluting the reduced polypeptide (or portions thereof) from the LC column.

These and other features of the applicant's teachings are set forth herein.

BRIEF DESCRIPTION OF THE DRAWINGS

The foregoing and other objects and advantages of the invention will be appreciated more fully from the following further description, with reference to the accompanying drawings. The skilled person in the art will understand that the drawings, described below, are for illustration purposes only. The drawings are not intended to limit the scope of the applicant's teachings in any way.

DETAILED DESCRIPTION

It will be appreciated that for clarity, the following discussion will explicate various aspects of embodiments of the applicant's teachings, while omitting certain specific details wherever convenient or appropriate to do so. For example, discussion of like or analogous features in alternative embodiments may be somewhat abbreviated. Well-known ideas or concepts may also for brevity not be discussed in any great detail. The skilled person will recognize that some embodiments of the applicant's teachings may not require certain of the specifically described details in every implementation, which are set forth herein only to provide a thorough understanding of the embodiments. Similarly it will be apparent that the described embodiments may be susceptible to alteration or variation according to common general knowledge without departing from the scope of the disclosure. The following detailed description of embodiments is not to be regarded as limiting the scope of the applicant's teachings in any manner.

Methods and systems for on-line preparation of a sample for mass spectrometry are provided herein. In accordance with various aspects of applicant's teachings, the methods and systems can provide for the reduction of a polypeptide, for example, on a LC column, and in various aspects, the direct delivery an eluent containing the reduced polypeptide to a downstream mass spectrometer for detection thereof. As described in detail below, the exemplary methods can thus improve processing time, efficiency, and/or reproducibility relative to conventional sample preparation protocols. For example, in various aspects, the methods and systems described herein can reduce and/or eliminate common sample preparation steps typically used in the preparation of polypeptides for mass spectrometric analysis such as the need to incubate the reducing agent with the polypeptide. Additionally or alternatively, in various aspects, the methods and systems described herein do not require exposing the reduced polypeptide to an alkylating agent to block thiol groups and prevent reformation of the disulfide bridges, for example. Full automation to enable high throughput polypeptide reduction and subsequent mass spectrometric detection thereof, for example, may increase the throughput relative to known techniques, while decreasing the expense and possibility for errors in typical peptide reduction sample preparation methods.

In some aspects, the methods and systems for an on-line preparation of a sample for mass spectrometry comprise introducing a sample containing a polypeptide having at least one disulfide bond to a liquid chromatography column. It will further be appreciated that any sample containing or suspected of containing one or more polypeptides having disulfide bridges can be used in accordance with the present teachings, including a sample of blood, plasma, serum, urine or saliva. Further, the sample can contain free polypeptides (e.g., a previously purified sample of polypeptides to be analyzed).

As used herein, "polypeptide" refers to any molecule comprising two or more amino acids having at least one peptide bond. For example, a polypeptide can comprise any peptide. Examples of peptides include, but is not limited to, tachykinin peptides, vasoactive intestinal peptides, pancreatic polypeptides, opioid peptides, calcitonin peptides, B-type natriuretic peptide, and peptide hormones. One exemplary peptide hormone is insulin. A polypeptide can also comprise, for example, a protein, an enzyme, or an antibody (e.g., a monoclonal antibody). The polypeptide can be intact or digested before being introduced to a liquid chromatography column. Methods for digestion or denaturing a polypeptide are known to those of ordinary skill in art and can comprise, for example, the use of trypsin (e.g., trypsinization), chymotrypsin, LysC, Arg-C, AspN, urea, sodium dodecyl sulfate (SDS), etc. Methods for labeling a polypeptide or protein prior to digestion or direct reduction in accordance with the present teachings can comprise, for example, labeling with iTRAQ, mTRAQ, iCAT, etc. In various aspects of the present teachings, the polypeptide can include at least one disulfide bond (e.g., 2 or more, 3 or more, 4 or more, 5 or more, 6 or more, 7 or more, 8 or more, 9 or more, or 10 or more disulfide bonds). Some or all of the disulfide bonds may be capable of being reduced by a reducing agent.

The exemplary methods and systems described herein for on-line preparation of a sample can also comprise retaining the polypeptide on a LC column. LC columns for use in accordance with the present teachings can have a variety of configurations.

For example, it will be appreciated by a person skilled in the art that a sample comprising one or more polypeptides can be loaded or introduced onto the LC column using known techniques such that the polypeptide is retained on the column (e.g., the solid phase). For example, the sample comprising the polypeptide can be loaded onto the column at a sample flow rate (e.g., about 5 µl/min, about 50 µl/min, about 100 µl/min, about 200 µl/min, about 300 µl/min, about 400 µl/min, about 500 µl/min, or greater than about 500 µl/min).

LC columns for use in accordance with the present teachings can have a variety of dimension, for example, an internal diameter of about 0.3 mm, about 0.5 mm, about 1 mm, about 2 mm, or about 3 mm, though other sized columns can be used, for example, depending on the application and sample preparation required.

After the sample comprising a polypeptide has been introduced to the liquid chromatography column, a solution comprising a reducing agent is flowed through the column. The reducing agent reduces (cleaves) one or more of the disulfide bonds of the retained polypeptide. The solution can comprise one or more known reducing agents, for example, a dithiol reducing agent such as DTT. Other reducing agents include, for example, tris(2-carboxyethyl)phosphine (TCEP), 2-mercaptoethanol (BME), 2-mercaptoethanolamine (2-MEA), etc. The solution comprising the reducing agent can be injected onto the column as a plug (e.g., a bolus of reducing agent). For example, the plug can be about 1 µl, about 5 µl, about 10 µl, about 20 µl, about 50 µl, about 100 µl, about 200 µl, about 500 µl, or about 1000 µl (1 ml).

In various aspects, the concentration of the reducing agent of the plug can be about 1 nM to about 1 M. By way of non-limiting example, the concentration of DTT in a reducing solution passed through the LC column can be about 1 mM, about 5 mM, about 10 mM, about 20 mM, about 30 mM, about 40 mM, about 50 mM, about 60 mM, about 70 mM, about 80 mM, about 90 mM, about 100 mM, or even greater.

In various aspects, the solution containing the reducing agent can be buffered, e.g., to be maintained at a certain pH. For example, a solution comprising DTT, though any reducing agent can be used, can be buffered such that the pH of the plug is between about 7 to about 9, and optimized for the reducing agent used. The buffered DTT, in this example, can comprise any number of buffers (e.g., ammonium bicarbonate), though additional buffers (e.g., ammonium acetate, ammonium formate, tris-HCL, etc.) can also be used to maintain the pH in a preferred range. It will also be appreciated in view of the present teachings that the concentration of the buffer (e.g., ammonium bicarbonate) can be varied to obtain a certain pH depending on the reducing agent and concentration of the reducing agent used. For example, a buffered solution of DTT can comprise about 1 mM to about 1000 mM ammonium bicarbonate.

In accordance with some aspects of the methods and systems described herein, the polypeptide can be reduced while retained on the LC column (e.g., after the solution comprising the reducing agent is introduced onto the liquid chromatography column) without an incubation period, though in some aspects, the flow rate may be reduced (but not stopped, i.e., not off-line) so that the retained peptide and the reducing agent can further interact with each other.

Additionally or alternatively, the methods and systems described herein also reduce or eliminate the need for the addition or introduction of an alkylating agent to the liquid chromatography column following polypeptide reduction. An example of an alkylating agent iodoacetamide. Other examples of thiol capping agents include, for example, iodoacetic acid. For example, the acidic pH of the eluent that follows the reducing agent can be effective to stabilize the reduced polypeptide so as to prevent the reformation of the disulfide bridges. It should also be appreciated that the composition and/or pH of the eluent can be adjusted such that reduced polypeptide are eluted from the liquid chromatography column. In some aspects, for example, the eluent can have a pH of less than about 7 (e.g., an acidic pH). For example, due to the presence of a reducing agent containing DTT and buffered with ammonium bicarbonate, there can be a transient increase in pH from the introduction of the solution comprising the reducing agent (e.g., a 50 µl plug of DTT dissolved in 500 mM ammonium bicarbonate) to the LC column.

In various aspects of the present teachings, the solution containing the reducing agent can be injected or introduced to the LC column at a first flow rate that is the same or different as the sample or analytical fluid flow rate described herein. For example, in some aspects, the flow rate of the solution containing the reducing agent can be less than the sample or analytical fluid flow rate. For example, the first flow rate can be about 25%, about 50%, about 75%, or about 100% (e.g., about the same rate) of the sample or analytical fluid flow rate. By way of non-limiting example, the first flow rate can be reduced to about 25% of the sample flow rate for loading the column (e.g., while still maintaining a positive fluid flow through the LC column) for about one minute so as to lead to a more complete reduction of the polypeptide retained on the LC column. In other aspects, the first flow rate can be about 1 µl/min, about 5 µl/min, about 10 µl/min, about 20 µl/min, about 50 µl/min, about 100 µl/min, about 200 µl/min, about 300 µl/min, about 400 µl/min, about 500 µl/min, or greater than about 500 µl/min. In various aspects, the first flow rate can be substantially maintained at a non-zero flow rate (i.e., greater than zero) during exposure to the reducing agent such that the system is operating under "on-line" conditions.

After flowing or introducing the solution comprising the reducing agent to the liquid chromatography column, an eluent is flowed through the liquid chromatography column to elute the reduced polypeptide from the liquid chromatography column. The eluent is flowed through the liquid chromatography column at a second flow rate (i.e., an analytical flow rate) that can be delivered with the eluted compounds to the ion source for ionization thereby. In some aspects the second, analytical flow rate can be about the same rate as the sample flow rate described above. For example, the second flow rate can be about 5 µl/min, about 50 µl/min about 100 µl/min, about 200 µl/min, about 300 µl/min, about 400 µl/min, about 500 µl/min, or greater than about 500 µl/min. In some aspects, the second flow rate is greater than the first flow rate. In another aspect, the second flow rate is about the same as the first flow rate. It will be appreciated in view of the present teachings that the eluent can comprise a variety of compositions configured to elute the reduced polypeptide from the LC column, with the eluate, containing the reduced polypeptide, being delivered to an ion source of a mass spectrometer for analysis, for example. In one exemplary aspect, the eluent can comprise a mobile phase of water and formic acid or a mobile phase gradient.

One of ordinary skill in the art will readily appreciate that one or more conditions under which the methods and systems described herein can be adjusted or optimized for the on-line reduction of a polypeptide in accordance with the present teachings. For example, in some aspects, the volume or concentration of reducing agent that is injected into the column can be adjusted to reduce some or all of the disulfide bonds in the polypeptide. In some aspects, for example, the amount of reducing agent can be in excess, relative to the number of disulfide bonds capable of being reduced. In one aspect, the concentration of DTT can be greater than about 10 mM, greater than about 20 mM, greater than about 30 mM, greater than about 40 mM, greater than about 50 mM, greater than about 60 mM, greater than about 70 mM, or greater than about 80 mM, all by way of non-limiting example.

In conventional techniques, incubation of the polypeptide containing a disulfide bond with a reducing agent typically occurs at or about room temperature. Applicant has achieved significantly reduced sample preparation time, however, by performing the reduction in the absence of stop flow conditions and at elevated temperatures (e.g., greater than 37° C., in a range from about 65° C. to about 75° C.). In accordance with various aspects of the present teachings, it will be appreciated that the temperature of the LC column can be adjusted, for example, by utilizing an LC heater or oven, or alternatively or additionally, by adjusting the temperature of the solutions being flowed therethrough. For example, the temperature of the LC column can be maintained at about 40° C. to about 90° C. during the reduction of the polypeptide in accordance with the present teachings. In other aspects, the temperature of the chromatography column is about 40° C., about 50° C., about 55° C., about 60° C., about 65° C., about 70° C., or about 75° C.

Other conditions such as, for example, reaction time and accessibility to disulfide bonds can affect the amount of partially reduced polypeptides.

Figure 3:
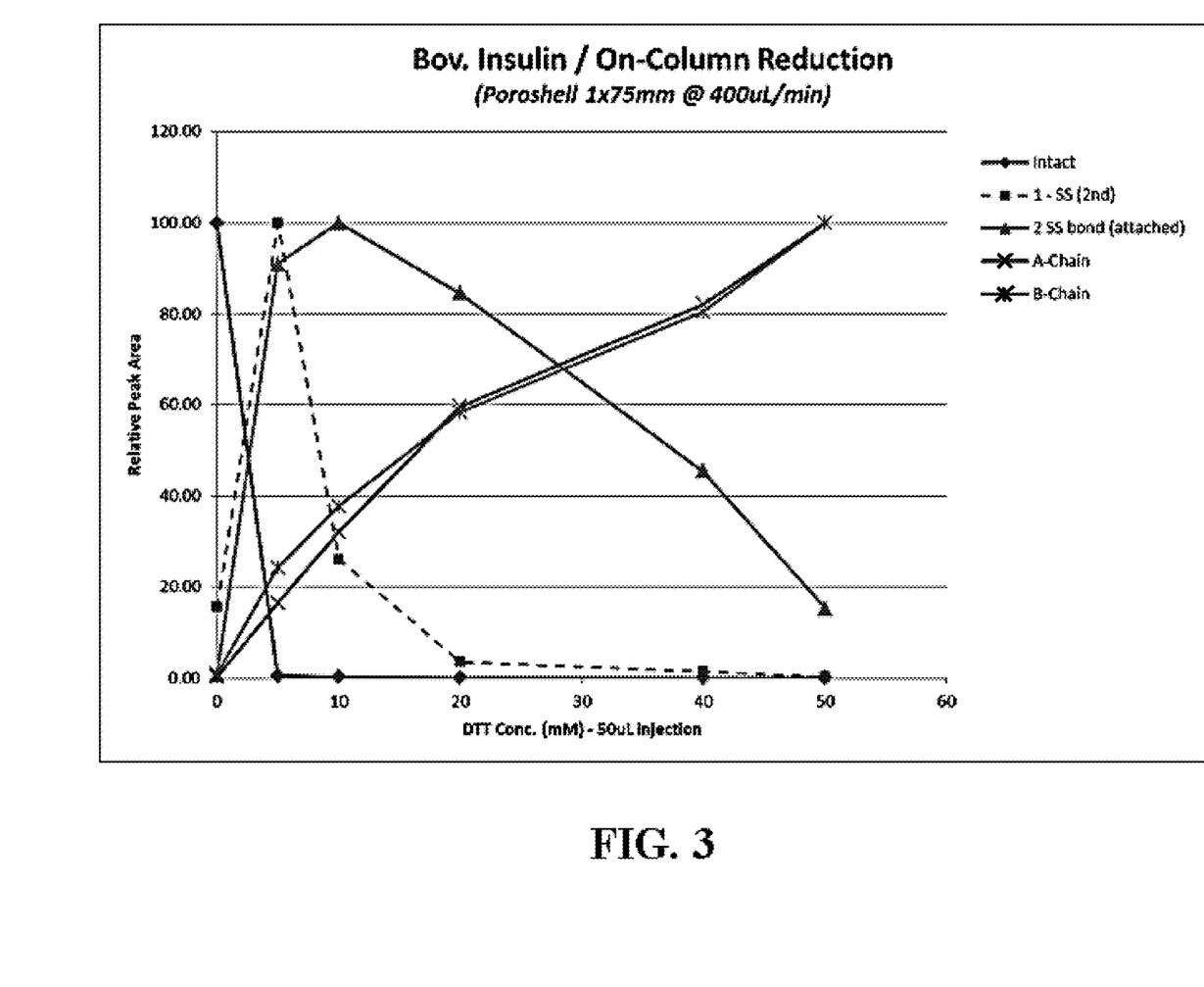
FIG. 3 depicts exemplary data for various insulin species using an on-line liquid chromatography reduction and mass spectrometry analysis.
Figure 4A:
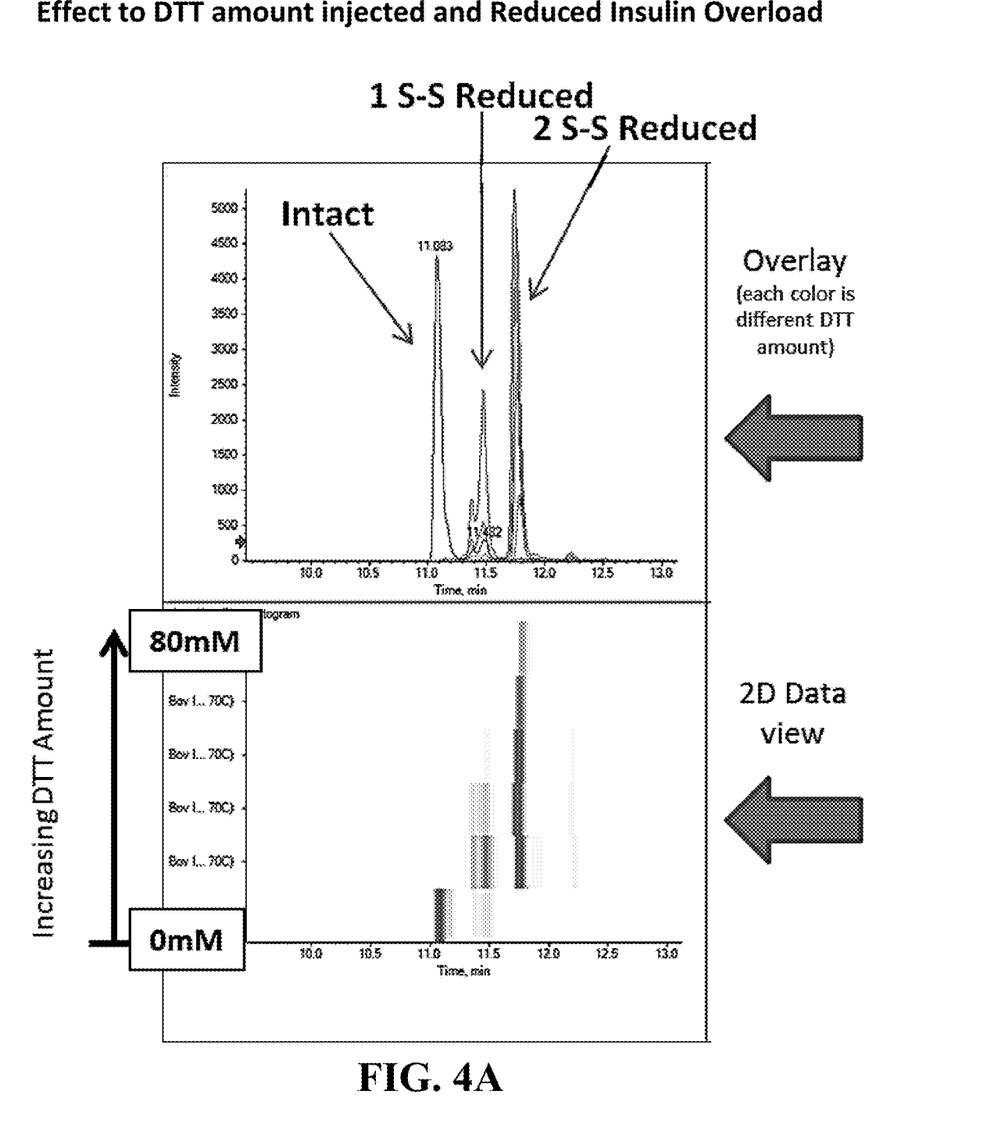
FIGS. 4A-C depict exemplary data for the amount of reducing agent injected and amount of reduced insulin observed using mass spectrometry.
Figure 4B:
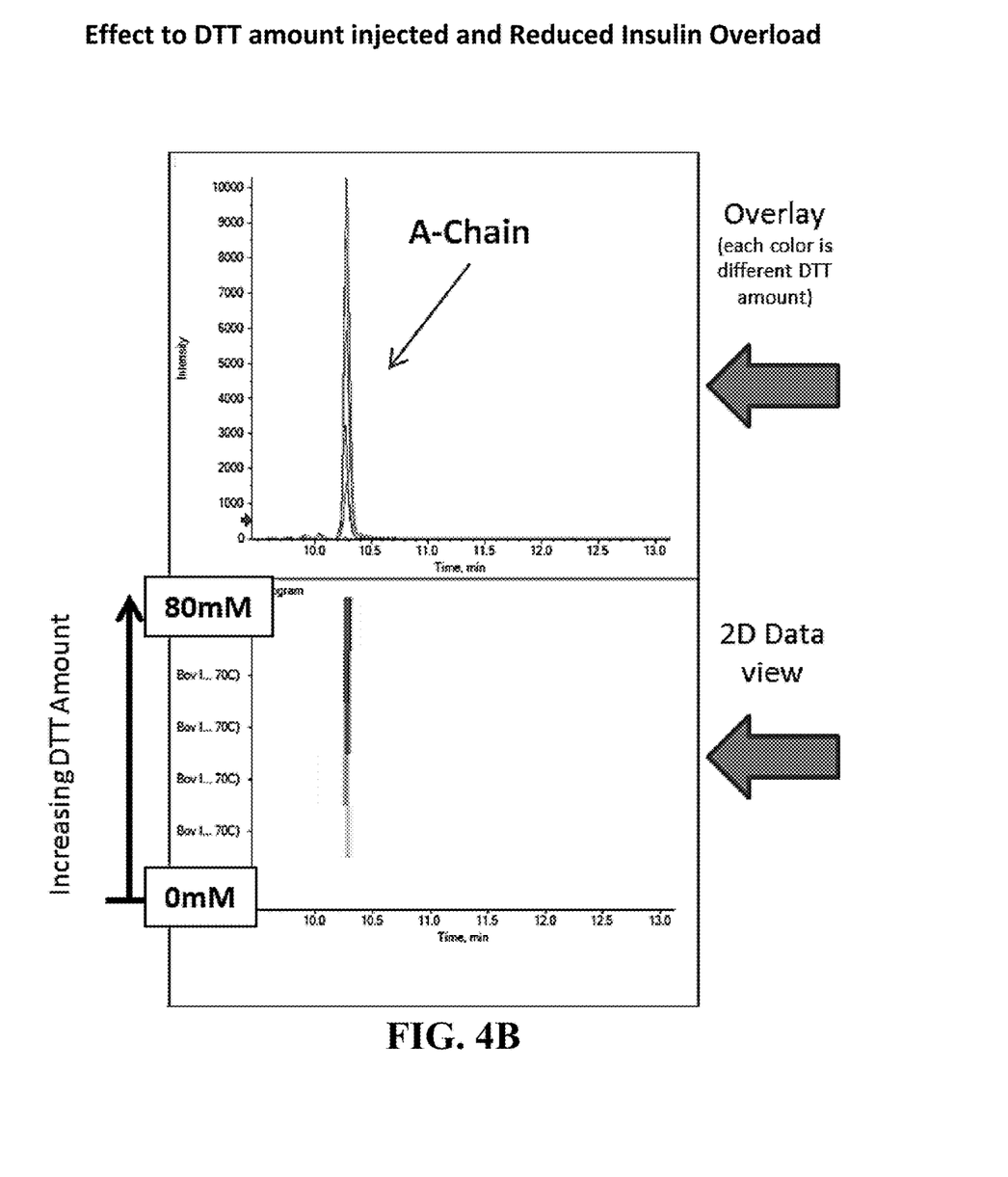
Figure 4C:
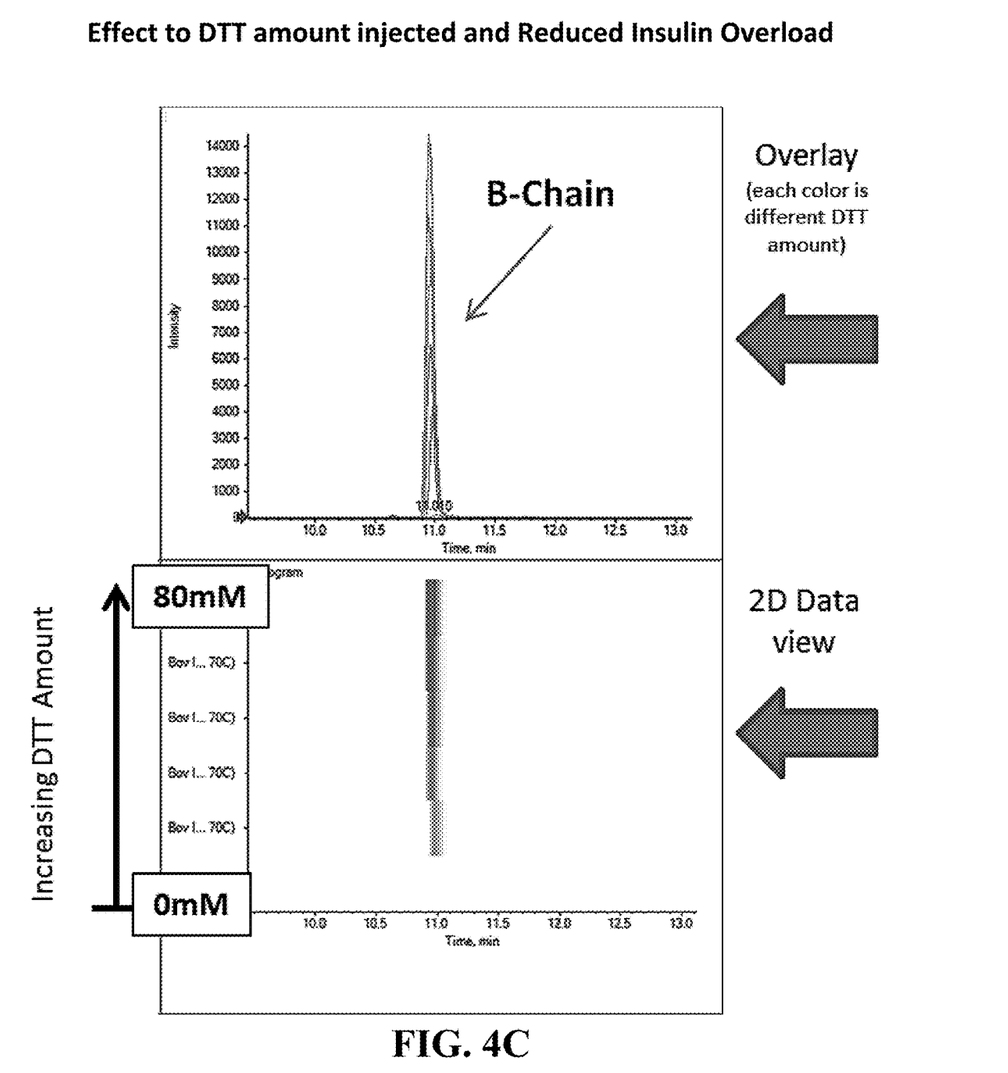

The applicant's teachings can be even more fully understood with reference to the following examples and data presented in FIGS. 3-4, which are provided to demonstrate but not limit the present teachings. As described below, an exemplary rapid and high-throughput on-line sample preparation workflow for cleavage of disulfide bonds within a polypeptide is provided in which all preparation steps can be easily performed on the LC column under non stop-flow conditions (i.e., without incubation). It is noted that in the exemplary workflows described below, the polypeptide is reduced and subsequently eluted and delivered to the ion source of the mass spectrometer without the addition of an alkylating agent such as iodoacetamide, which is generally part of conventional preparation methods.

Other embodiments of the applicant's teachings will be apparent to those skilled in the art from consideration of the present specification and practice of the present teachings disclosed herein. It should be appreciated by those skilled in the art in light of the present teachings that adjustments can be made to the volumes, concentrations, temperatures and flow rates described below, for example, to obtain optimum results in accordance with the present teachings. It is intended that these examples be considered as exemplary only.

EXAMPLES

Example 1—Methods for On-Line Reduction of a Polypeptide

Figure 1:
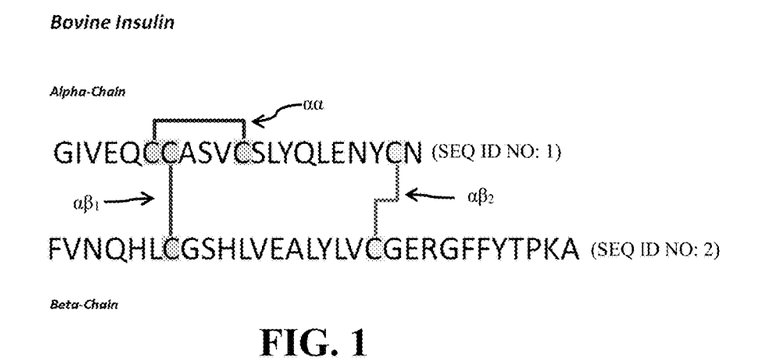
FIG. 1, in schematic diagram, depicts the amino acid sequence and disulfide bonds in a bovine insulin molecule.

Insulin was used as a model system for a small protein (e.g., peptide hormone). The reduction of one, two, or three disulfide bonds between cysteine (C or Cys) residues within the insulin molecule was examined. Referring to FIG. 1, the amino acid sequence for bovine insulin is shown. Insulin (including insulin analogues) comprise two peptide chains (an α-chain and a β-chain), which generally exhibit two disulfide bridges between cysteine residues linking the α-chain to the β-chain ($\alpha\beta_1$ and $\alpha\beta_2$), and one intra-chain (α-chain) disulfide bridge. The molecular weight of insulin is about 5400 to about 5900 kDa.

Figure 2:
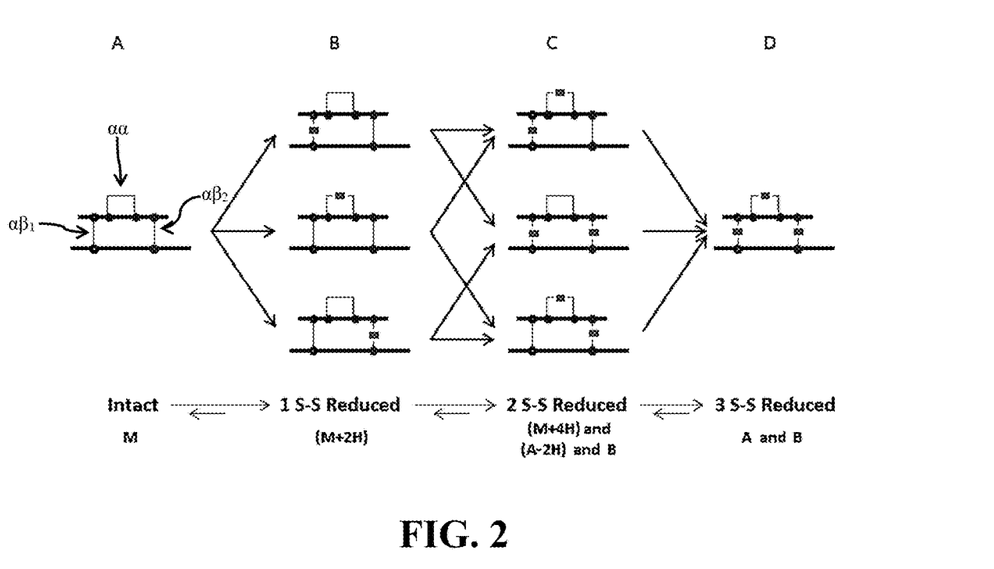
FIG. 2 depicts various exemplary reductions of the disulfide bonds in an insulin molecule.

Referring now to FIG. 2, an insulin molecule can be partially or completely reduced as depicted in panels B, C, and D. Each of the intact three disulfide bonds in insulin are represented schematically under panel A (two disulfide bonds linking the alpha chain to the beta chain and one intra-chain disulfide bond). A reduction can occur at any of the three disulfide bonds, resulting in three reduced insulin molecules (panel B). A disulfide bond that has been reduced is represented as a box. A reduction of a second disulfide bond leads to three additional types of reduced insulin molecules (panel C). There are therefore a total of six types of partially reduced insulin molecules (panels B and C). Finally, a completely reduced insulin molecule would have each of the three disulfide bonds reduced, as shown in panel D.

An on-line or on-column reduction method in accordance with various aspects of the present teachings was used to reduce an insulin molecule within a LC-MS system. A sample comprising insulin in a 98% aqueous with 0.1% acid (e.g., formic acid) solution was first injected onto a LC column such that the insulin could be loaded onto the columns (e.g., associated with the solid phase). For loading, the sample (liquid phase) flow rate was maintained at greater than 200 µl/min for about 1 minute on a 2 mm column. Liquid chromatography columns having an internal diameter from 1 mm to 3 mm at various flow rates and temperatures were tested including: Poroshell 1×75 mm at 400 µl/min and 70° C., Aries 2×150 mm at 250 µl/min and 70° C., and Zorbax 2×100 mm at 300 µl/min and 65° C. The LC column was operated at a temperature of greater than 40° C. in all cases.

After insulin loading, a buffered solution (e.g., containing 500 mM ammonium bicarbonate) comprising various concentrations of dithiothreitol ("DTT") was then injected through the LC column at various flow rates. The DTT solution was injected as a plug (e.g., a 50 µl plug), with the buffer temporarily raising the pH of the LC column as it flowed therethrough. To elute the reduced polypeptide following the addition of the DTT, the flow rate was maintained at analytical conditions (e.g., greater than about 200 µl/min) with the mobile phase lowering the pH of the column. It will be appreciated that the organic content of the eluent can also be raised to ensure elution of all polypeptides. In the example presented, the organic solvent used was acetonitrile (ACN) containing 0.1% formic acid, though other organic solvents such as methanol (MeOH), isopropanol (IPA), or mixtures of ACN, MeOH and IPA could also be used.

The eluent was subsequently ionized and analyzed via MS to detect the relative concentrations of the non-reduced and reduced insulin. Ionization was achieved with a TurboV ion source operated in positive mode. The nebulizing gas (GAS 1), the drying gas (GAS 2) and temperature were set at 40 psi, 80 psi and 550° C., respectively. A triple TOF 5600 instrument was use for analysis (operated in positive mode, acquiring data from m/z 250 to 2000.

With reference now to FIG. 3, exemplary data for the various species of reduced insulin is depicted in the Poroshell 1×75 mm operated at 70° C., as the concentration of DTT in the 50 μL plug was increased from 0 mM to 50 mM (flow rate was maintained at 400 μL throughout loading, reduction, and elution). At low DTT concentrations (e.g., 5-10 mM), the relative amount of intact insulin (with no reduced disulfide bonds) quickly decreased, while the relative amount of singly (1 S—S) and doubly (2 S—S) reduced disulfide fractions increased. Almost complete reduction of the insulin molecule (shown at the isolated A-chain and B-chain) was obtained at about 50 mM (i.e., no intact or singly-reduced insulin detected, relatively limited doubly-reduced insulin detected). Accordingly, the complete reduction of an exemplary polypeptide (i.e., insulin) was achieved directly on a LC column while flowing at or near analytical conditions (e.g., on-line reduction), without incubation or the addition of an alkylating agent such as iodoacetamide. While increasing the concentration of DTT increased the efficiency of reduction of insulin as demonstrated in FIG. 3, it is also noted that improved reduction can be obtained, for example, by increasing the temperature of the LC column and/or by temporarily reducing the flow rate of the mobile phase to a non-zero flow rate (e.g., about 25% of the analytical flow rate) for about one minute following introduction of the reducing agent.

With reference now to FIG. 4, shows that with increasing amount of DTT used, (y-axis for bottom chart of each of FIGS. 4A-C) a decrease of the intact insulin was observed, as well as the intermediate singly- and doubly-disulfide reduced species. Also observed is an increase of the amount of detected individuals chains (e.g., A-chain and B-chain). The top chart of each of FIGS. 4A-C shows the same data in an overlay fashion (XIC of all form of insulin).

Figure 5:
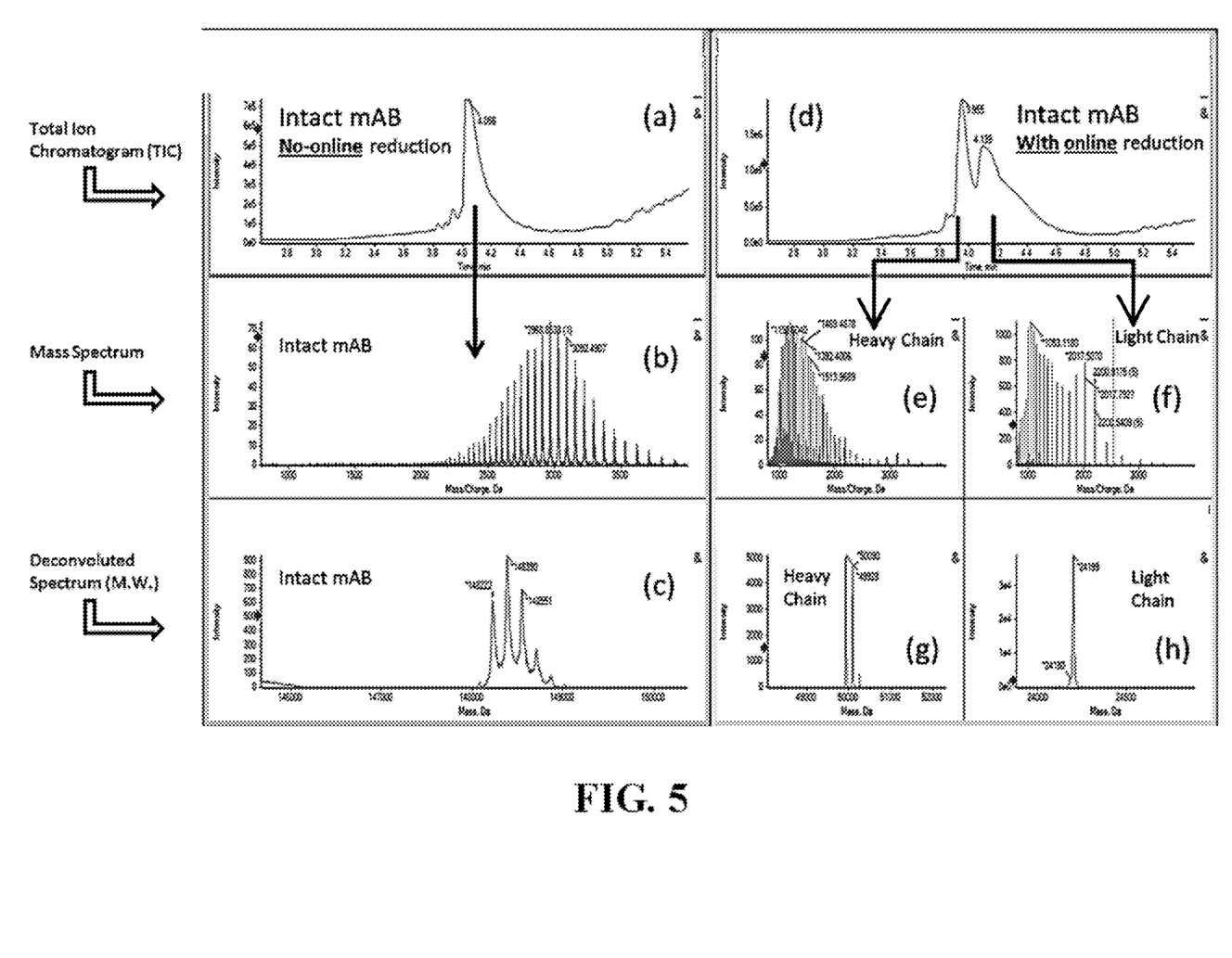
FIGS. 5A-H depict exemplary data for various peptides with and without on-column reduction of a monoclonal antibody (mAB) observed using mass spectrometry.

With reference now to FIG. 5, similar data demonstrating on-column reduction of monoclonal antibodies (mAB) is particularly depicted in FIGS. 5D-H, in which both heavy chain and the light chain were produced and detected following on-line reduction of the mAB in accordance with various aspects of the present teachings. When no reducing agent was injected into the LC column, however, the intact mAB was detected (FIGS. 5A-C).

Figure 6:
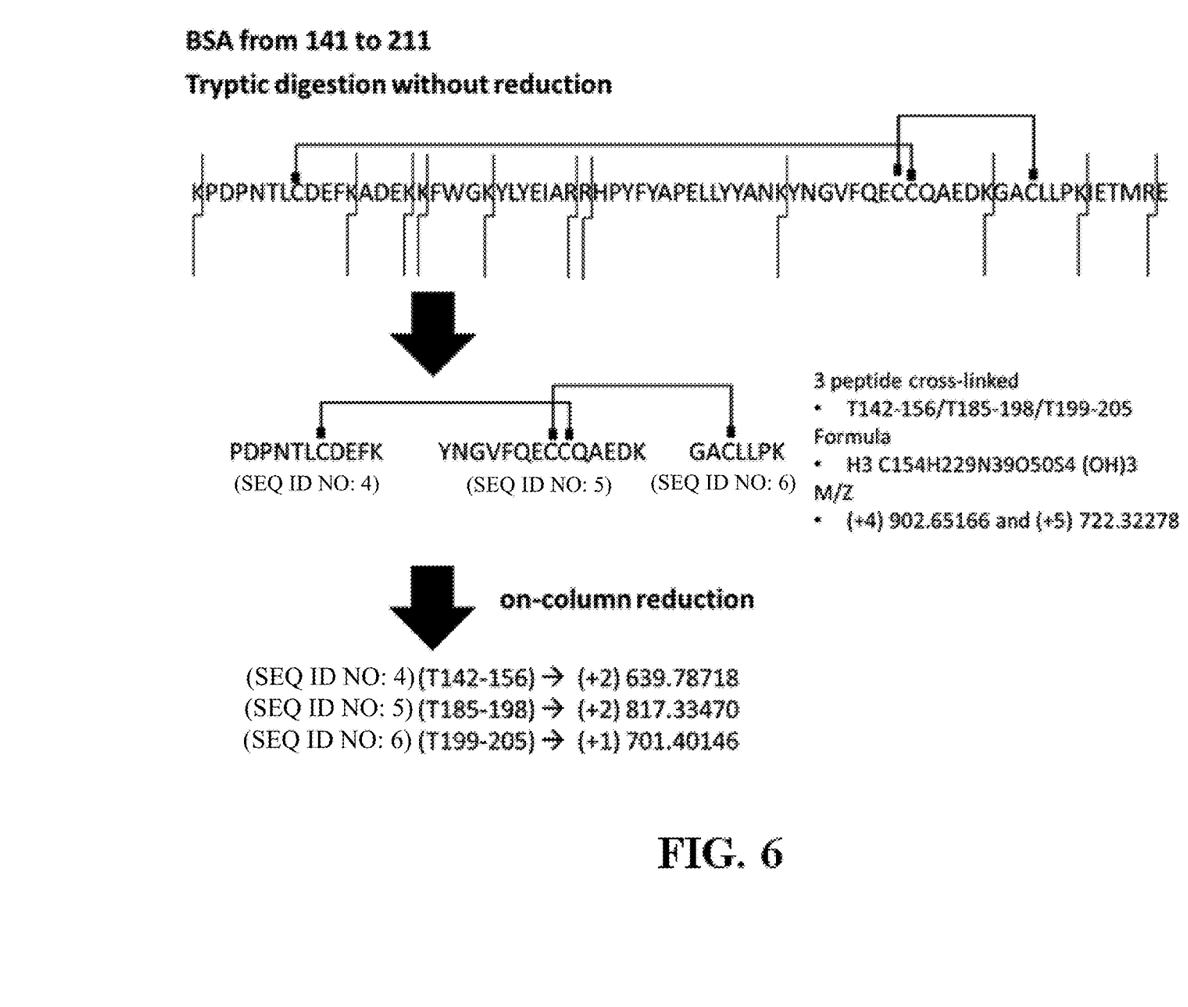
FIG. 6 depicts various exemplary peptides resulting from tryptic digestion and on-line reduction of bovine serum albumin (BSA).
Figure 7:
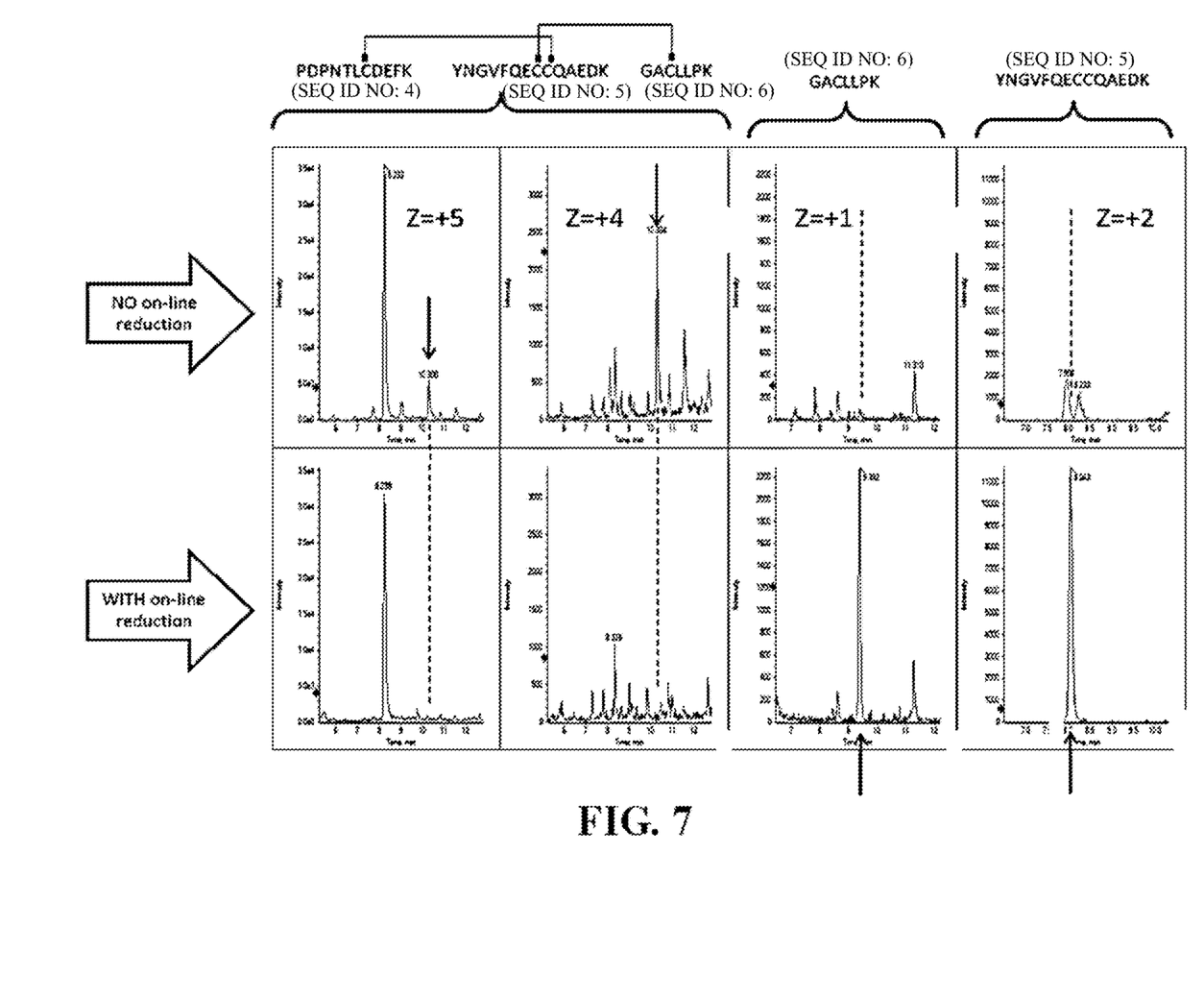
FIG. 7 depicts exemplary data for various peptides following tryptic digestion and with and without on-column reduction of BSA observed using mass spectrometry.

Additionally, using methods in accordance with the present teachings, on-column reduction of a protein digest that did not undergo reduction prior to digestion with trypsin has also been demonstrated. With reference now to FIGS. 6-7, bovine serum albumin (BSA), which contains a total of 17 disulfide bonds, was used as an exemplary model. As shown in FIG. 6, two disulfide bonds are found in the amino acid sequence of BSA between position 141 and 211. Upon digestion with trypsin (assuming no prior reduction and complete cleavage at lysine), three short peptides cross-linked with disulfide bonds are created. Upon further, on-line reduction in accordance with various aspects of the present teachings, up to three individual peptides are generated. With reference to FIG. 7, it is possible to detect the intact cross-linked peptide when the digest is analyzed intact (T142-152/T185-198/T199-205). When on-line reduction is performed using DTT, the individual peptides (T199-205 and T185-199) are detected independently (as shown in the two right columns of the bottom row, respectively). As demonstrated in the two left columns of the bottom row, which do not exhibit a signal at the +4 and +5 charge states of the intact peptide, it will be appreciated that the intact peptide was not detected after on-line reduction, thus suggesting complete reduction under experimental conditions. It should also be noted that reduced peptides were not detected or observed when the intact sample was analyzed, as shown in the two right columns of the top row.

The section headings used herein are for organizational purposes only and are not to be construed as limiting. While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of skill in the art.

The invention claimed is:

1. A method for on-line preparation of a sample for mass spectrometry analysis comprising:
   a. introducing a sample comprising a polypeptide having at least one disulfide bond to a liquid chromatography column;
   b. retaining the polypeptide on the liquid chromatography column;
   c. flowing a solution comprising a reducing agent continuously through the liquid chromatography column so as to cleave one or more of the at least one disulfide bonds of the retained polypeptide while the reducing solution is flowed therethrough;
   d. flowing an eluent continuously through the liquid chromatography column so as to elute the reduced polypeptide from the liquid chromatography column as an eluate, the eluant comprising a mobile phase gradient and wherein the eluent is flowed through the liquid chromatography column without having exposed the reduced polypeptide to an alkylating agent; and
   e. delivering the eluate containing the reduced polypeptide to an ion source of a mass spectrometer.

2. The method of claim 1, wherein the solution comprising the reducing agent is flowed through the liquid chromatography column at a first flow rate and the eluent is flowed through the liquid chromatography column at a second flow rate, wherein the second flow rate is greater than the first flow rate.

3. The method of claim 2, wherein the first flow rate and the second flow rate are each 50 µl/min to 500 µl/min.

4. The method of claim 1, wherein the method lacks an incubation period after introducing the reducing solution into the liquid chromatography column.

5. The method of claim 1, wherein flowing the solution comprising the reducing agent comprises introducing a plug of dithiothreitol into a fluid stream flowing through the liquid chromatography column at a first flow rate.

6. The method of claim 5, wherein the solution comprising the reducing agent is buffered.

7. The method of claim 1, wherein the pH of the eluent is less than 7.

8. The method of claim 1, wherein the temperature of the liquid chromatography column is greater than 40° C.

9. The method of claim 1, wherein the polypeptide comprises a protein.

10. The method of claim 9, wherein the protein comprises an enzyme.

11. The method of claim 9, wherein the protein comprises insulin.

12. The method of claim 1, wherein the polypeptide comprises an antibody.

13. The method of claim 1, wherein the polypeptide comprises an antibody drug conjugate.

14. The method of claim 1, wherein the liquid chromatography column is 0.3 mm to 3 mm in diameter.

15. The method of claim 1, wherein the reducing agent comprises one or more of a dithiol reducing agent, tris(2-carboxyethyl)phosphine (TCEP), 2-mercaptoethanol (BME), and 2-mercaptoethanolamine (2-MEA).

16. A method of preparing a sample for mass spectrometry analysis comprising:

a. introducing a sample comprising a polypeptide to a liquid chromatography column;
b. retaining the polypeptide on the liquid chromatography column;
c. reducing the polypeptide by a reducing agent; wherein the polypeptide comprises one or more disulfide bonds capable of being reduced; and wherein reducing the polypeptide comprises:
   i. flowing a solution comprising the reducing agent continuously through the liquid chromatography column at a first flow rate; and
   ii. flowing an eluent continuously through the liquid chromatography column so as to elute the reduced polypeptide as an eluate from the liquid chromatography column at a second flow rate; wherein the second flow rate is greater than the first flow rate and the eluent comprises a mobile phase gradient; and
d. delivering the eluate from a liquid chromatography column comprising the reduced polypeptide to a mass spectrometer without subjecting the reduced polypeptide to an alkylation step.

17. The method of claim 6 wherein the pH of the buffered solution is between 7 and 8.

18. The method of claim 8 wherein the temperature is 60° C. to 75° C.

19. The method of claim 16 wherein the step of reducing the polypeptide by a reducing agent is performed at a temperature of between 40° C. and 90° C.

* * * * *

SEQUENCE LISTING

```
<160> NUMBER OF SEQ ID NOS: 6

<210> SEQ ID NO 1
<211> LENGTH: 21
<212> TYPE: PRT
<213> ORGANISM: Bos taurus

<400> SEQUENCE: 1

Gly Ile Val Glu Gln Cys Cys Ala Ser Val Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Bos taurus

<400> SEQUENCE: 2

Phe Val Asn Gln His Leu Cys Gly Ser His Leu Val Glu Ala Leu Tyr
1               5                   10                  15
```

```
Leu Val Cys Gly Glu Arg Gly Phe Phe Tyr Thr Pro Lys Ala
            20                  25                  30

<210> SEQ ID NO 3
<211> LENGTH: 71
<212> TYPE: PRT
<213> ORGANISM: Bos taurus

<400> SEQUENCE: 3

Lys Pro Asp Pro Asn Thr Leu Cys Asp Glu Phe Lys Ala Asp Glu Lys
1               5                   10                  15

Lys Phe Trp Gly Lys Tyr Leu Tyr Glu Ile Ala Arg Arg His Pro Tyr
                20                  25                  30

Phe Tyr Ala Pro Glu Leu Leu Tyr Tyr Ala Asn Lys Tyr Asn Gly Val
            35                  40                  45

Phe Gln Glu Cys Cys Gln Ala Glu Asp Lys Gly Ala Cys Leu Leu Pro
        50                  55                  60

Lys Ile Glu Thr Met Arg Glu
65                  70

<210> SEQ ID NO 4
<211> LENGTH: 11
<212> TYPE: PRT
<213> ORGANISM: Bos taurus

<400> SEQUENCE: 4

Pro Asp Pro Asn Thr Leu Cys Asp Glu Phe Lys
1               5                   10

<210> SEQ ID NO 5
<211> LENGTH: 14
<212> TYPE: PRT
<213> ORGANISM: Bos taurus

<400> SEQUENCE: 5

Tyr Asn Gly Val Phe Gln Glu Cys Cys Gln Ala Glu Asp Lys
1               5                   10

<210> SEQ ID NO 6
<211> LENGTH: 7
<212> TYPE: PRT
<213> ORGANISM: Bos taurus

<400> SEQUENCE: 6

Gly Ala Cys Leu Leu Pro Lys
1               5
```